United States Patent
Nelson et al.

(10) Patent No.: US 6,986,769 B2
(45) Date of Patent: Jan. 17, 2006

(54) ABLATION CATHETER WITH COOLED LINEAR ELECTRODE

(75) Inventors: Dale Nelson, Minneapolis, MN (US); Steven D. Savage, Paynesville, MN (US); William Penny, Arden Hill, MN (US); Jeffrey Santer, Spring Lake Park, MN (US)

(73) Assignee: Biosense Webster, Inc., Diamond Bar, CA (US)

( * ) Notice: Subject to any disclaimer, the term of this patent is extended or adjusted under 35 U.S.C. 154(b) by 0 days.

(21) Appl. No.: 10/657,647

(22) Filed: Sep. 8, 2003

(65) Prior Publication Data

US 2004/0054369 A1 Mar. 18, 2004

Related U.S. Application Data

(62) Division of application No. 09/642,202, filed on Aug. 21, 2000, now Pat. No. 6,669,692.

(51) Int. Cl.
*A61B 18/18* (2006.01)
(52) U.S. Cl. .............. 606/41; 606/47; 606/129
(58) Field of Classification Search ............. 606/41, 606/48, 49, 50, 34, 46, 47; 607/101, 104–106, 607/115, 116, 120
See application file for complete search history.

(56) References Cited

U.S. PATENT DOCUMENTS

| | | | |
|---|---|---|---|
| 5,531,685 A | | 7/1996 | Hemmer et al. |
| 5,643,197 A | * | 7/1997 | Brucker et al. ............. 604/20 |
| 5,755,760 A | * | 5/1998 | Maguire et al. ............ 607/122 |
| 5,800,482 A | * | 9/1998 | Pomeranz et al. .......... 607/101 |
| 5,913,854 A | * | 6/1999 | Maguire et al. ............ 606/41 |
| 5,913,856 A | * | 6/1999 | Chia et al. ................. 606/41 |
| 5,919,188 A | * | 7/1999 | Shearon et al. ............. 606/41 |
| 5,938,694 A | | 8/1999 | Jaraczewski et al. |
| 6,015,407 A | | 1/2000 | Reib et al. |
| 6,032,077 A | * | 2/2000 | Pomeranz ................. 607/101 |
| 6,083,222 A | | 7/2000 | Klein et al. |
| 6,113,556 A | | 9/2000 | Avitall |
| 6,212,434 B1 | | 4/2001 | Scheiner et al. |
| 6,224,587 B1 | | 5/2001 | Gibson |
| 6,425,894 B1 | | 7/2002 | Brucker et al. |
| 6,475,217 B1 | | 11/2002 | Platt |
| 6,522,930 B1 | | 2/2003 | Schaer et al. |
| 6,607,505 B1 | * | 8/2003 | Thompson et al. ...... 604/95.04 |

FOREIGN PATENT DOCUMENTS

| | | |
|---|---|---|
| EP | 0 856 292 A1 | 8/1998 |
| EP | 0928 601 A1 | 7/1999 |
| WO | WO 94/02077 | 3/1994 |
| WO | WO 99/56812 | 11/1999 |

* cited by examiner

*Primary Examiner*—Henry Bennett
*Assistant Examiner*—Camtu Nguyen
(74) *Attorney, Agent, or Firm*—George H. Gerstman; Seyfarth Shaw LLP

(57) ABSTRACT

The ablation catheter is comprised of a guiding catheter and an inner catheter. The guiding catheter is comprised of a shaft section which is attached to an articulating section at its distal end and a first handle at its proximal end. The inner catheter is comprised of an elongated central shaft, an electrode assembly attached to the distal end of the central shaft, and a second handle attached to the proximal end of the central shaft. The electrode assembly is comprised of a flexible plastic catheter tube having an outer surface, a porous tip electrode, and at least one linear electrode carried on the outer surface of the catheter tube. The electrode assembly is articulated to better align the electrode assembly to the generally arcuate shape of the inner chambers of the heart.

10 Claims, 5 Drawing Sheets

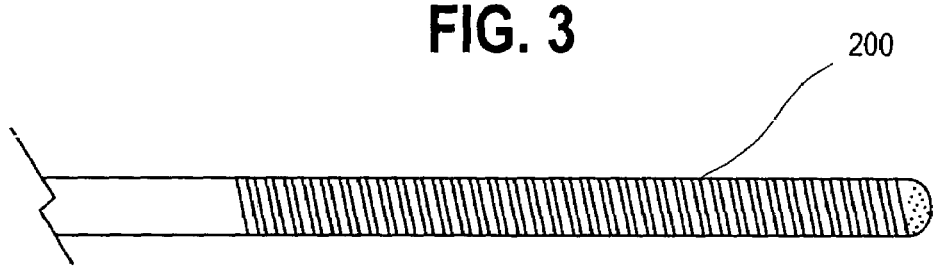
FIG. 3    200
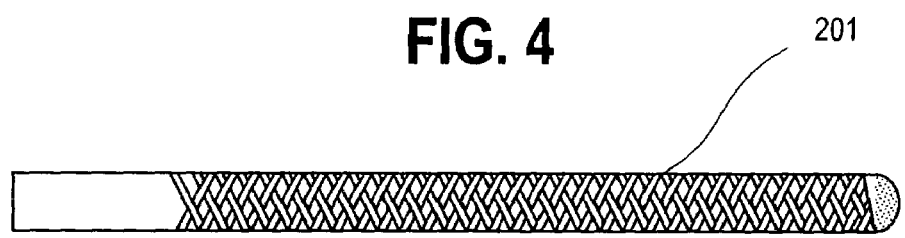
FIG. 4    201

ABLATION CATHETER WITH COOLED LINEAR ELECTRODE

This is a division of application Ser. No. 09/642,202 filed Aug. 21, 2000, now U.S. Pat. No. 6,669,692.

FIELD OF THE INVENTION

This invention relates generally to a cardiac catheter used for performing cardiovascular procedures on the heart. More particularly this invention relates to an ablation catheter used predominantly for treating cardiac arrhythmias.

BACKGROUND OF THE INVENTION

Radio frequency ablation (RFA) has become a common treatment for treating specific cardiac arrhythmias. Portions of the heart sometimes form alternative conduction pathways which interfere with the normal conduction of the electrical signals which regulate the beating of the heart thereby causing some cardiac arrhythmias to occur. In order to remove these alternative conduction pathways, the heart is first mapped through catheter mapping procedures in order to find where these alternative conduction pathways are located, and then RFA is used to prevent these areas of the heart from disrupting the normal conduction patterns of the heart.

RFA typically involves the use of a specialized ablation catheter which is positioned at the site of the alternative conduction pathway. Radio frequency (RF) waves are then typically delivered through the ablation catheter and onto the alternative conduction pathway. The radio frequency waves create heat at the site of the alternative conduction pathway creating a lesion which destroys the tissues forming the alternative conduction pathways.

Ablation catheters have been developed in order to deliver radio frequency waves at the site of the abnormal pathway. While some of these prior art ablation catheters are well suited for particular procedures, the ability of these prior art ablation catheters to perform a variety of procedures effectively have been limited due to a number structural constraints which are necessitated by the spatial and physiological requirements of the applications in which these ablation catheters are to be used. Size, flexibility, and maneuverability are common restraints which have previously prevented more effective ablation catheter designs.

One drawback to the prior art is their inability to make a variety of lesions. There are typically two types of lesions which are generated by ablation catheters. One type of lesion is a focal lesion where the RF wave is concentrated at a point. Typically, the prior art is limited to making focal lesions. A tip electrode carried on the distal tip of an ablation catheter is preferably used for making focal lesions. However, there are a variety of procedures in which linear lesions are preferred, requiring that the RF energy be delivered along a line. There are prior art ablation catheters which are capable of creating linear lesions; however, these prior art ablation catheters are not particularly suited for making focal lesions. A linear electrode is preferably utilized for making linear lesions. Although tip electrodes can also be used utilized for making linear lesions, the use of tip electrodes to make linear lesions can be significantly more difficult and time consuming.

The maneuverability of the prior art ablation catheters also limit their effectiveness. The ablation catheters are typically utilized within the interior chambers of the heart. The precise placement of the electrodes onto the site to which the RF waves are to be delivered and the sufficiency of the contact between an electrode and the site significantly impacts the effectiveness of the treatment. Linear electrodes, and especially longer linear electrodes, tend to be stiffer, making it more difficult for them to maneuver and to conform to the generally arcuate shape of the interior walls of the heart.

Another problem common amongst the prior art ablation catheters is the formation of coagulum around the electrode during ablation. The heat generated by the RFA sometimes causes the electrode to overheat causing the blood surrounding the electrode to coagulate on the electrode. As the coagulum collects on the electrode, the impedance between the electrode and the site to which the RF wave is applied increases, thereby reducing the effectiveness of the electrode. As a result it is often necessary to stop the RFA in order to remove the coagulum from the electrode.

Accordingly, it is an object of this invention to provide an ablation catheter which is capable of generating both focal lesions and linear lesions while having the appropriate size, flexibility and maneuverability to enable it to be used effectively in a variety of RFA procedures.

Accordingly, it is also an object of this invention to provide for an ablation catheter with a linear electrode which is easily maneuverable and conforms readily to the arcuate shape of the interior of the heart while still having the appropriate size, flexibility and maneuverability to enable the ablation catheter to be used effectively in a variety of RFA procedures.

Accordingly, it is also a further object of this invention to provide an ablation catheter with a means for cooling the electrode in order to reduce the rate at which the coagulum builds up on the surface of an electrode while still having the appropriate size, flexibility and maneuverability to enable it to be used effectively in most RFA procedures.

Other objects and advantages of the invention will become apparent as the description proceeds.

To achieve these objectives, and in accordance with the purposes of the present invention the following ablation catheter is presented. As will be described in greater detail hereinafter, the present invention provides the aforementioned and employs a number of novel features that render it highly advantageous over the prior art.

SUMMARY OF THE INVENTION

In accordance with an illustrative embodiment of the present invention, an ablation catheter is provided which comprises two major components, an articulating guiding catheter and an inner articulating catheter disposed therein. The guiding catheter is typically inserted into the vascular system and is guided and manipulated through the vascular system until it reaches the appropriate chamber of the heart. The inner catheter is disposed within the guiding catheter until a desired location in the heart is reached. At that point the inner catheter is then extended beyond the guiding catheter allowing the inner catheter to more precisely position itself onto a treatment site.

In an illustrative embodiment, the guiding catheter is comprised of a shaft section which is attached to an articulating section at its distal end and a first handle at its proximal end. The inner catheter is comprised of an elongated central shaft, an electrode assembly attached to the distal end of the central shaft, and a second handle attached to the proximal end of the central shaft.

In one embodiment, the electrode assembly is comprised of a flexible plastic catheter tube having an outer surface, a porous tip electrode, and at least one linear electrode carried on the outer surface of the catheter tube. The catheter tube is used to provide axial and radial stability to the electrode assembly and to provide a conduit to the electrode assembly. Fluid is distributed to the linear electrode and the porous tip electrode through a plurality of apertures extending from the inner surface of the catheter tube to the outer surface of the catheter tube.

The linear electrode is utilized in order to make linear lesions in the heart tissue. In one embodiment, the linear electrode is comprised of a tubular array of conductive metal strands carried on the outer surface of the catheter tube, the conductive strands extending along the catheter tube in a plurality of directions relative to the longitudinal axis of the catheter tube. In one embodiment, the tubular array of metal strands is a wound helical coil. In an alternate embodiment, the tubular array of metal strands is arranged in a braided construction. The porous tip electrode is located at the distal end of the electrode assembly. The tip electrode provides a means for creating lesions concentrated at particular points in the heart, otherwise called focal lesions.

Articulation of the electrode assembly is utilized in order to better align the linear electrode to the generally arcuate shape of the inner chambers of the heart. One means for articulating the electrode assembly is by extending a pull wire through the inner catheter and attaching it to the distal tip of the catheter tube. An alternate means for articulating the electrode assembly is achieved by running the pull wire through the inner catheter, then having the wire run externally along the linear electrode, and then finally attaching the pull wire to the distal tip of the electrode assembly. A second alternate means for articulating the electrode assembly is achieved through the use of a memory shaped tube which is thermally activated to conform to a predetermined shape upon reaching body temperature.

A more detailed explanation of the invention is provided in the following description and claims, and is illustrated in the accompanying drawings.

DESCRIPTION OF THE DRAWINGS

FIG. 3 is a side view of a linear electrode assembly having helically wound coils.

FIG. 4 is a side view of a linear electrode assembly having a braided construction.

DETAILED DESCRIPTION OF ILLUSTRATIVE EMBODIMENTS

Figure 1:
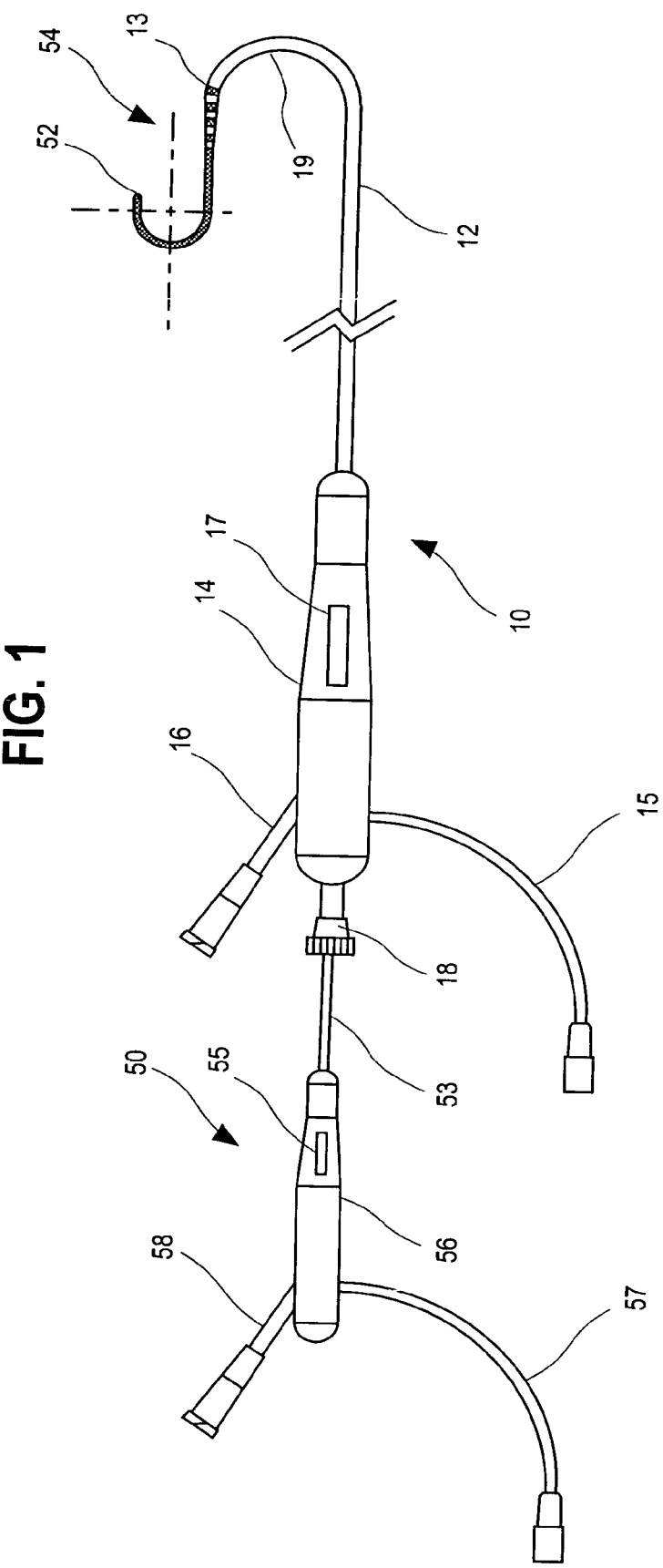
FIG. 1 is a planar view of an ablation catheter embodying features in accordance with the present invention.

Referring to FIG. 1, an ablation catheter is comprised of two major components, an articulating guiding catheter 10 and an inner articulating catheter 50 disposed therein. The guiding catheter 10 is typically inserted into the vascular system and is guided and manipulated through the vascular system until it reaches the appropriate chamber of the heart. Once positioned within the heart, the guiding catheter 10 provides a uniform conduit for introducing the inner catheter 50 into the chambers of the heart. The inner catheter 50 is disposed within the guiding catheter and typically travels within the guiding catheter until a desired location in the heart is reached. At that point the inner catheter 50 is then extended beyond the guiding catheter 10 allowing the inner catheter 50 to more precisely position itself onto a treatment site.

The guiding catheter 10 is comprised of a shaft section 12 having an articulating section 19 at its distal end and a first handle 14 attached at its proximal end. A plurality of ring electrodes 13 is carried on the distal end of the guiding catheter 10. The ring electrodes 13, when in contact with the heart tissue, are able to take measurements of endocardial potentials. The shaft 12 is comprised of preferably constructed of an inner and outer layer of plastic which encapsulate a braided metal, but other means of constructing the shaft would work suitably with the present invention. The handle 14 is comprised of a first mechanism for articulating 17 the articulating section 19, an interface for electricity 15, a first fluid interface 16, and an interface for inserting 18 the inner articulating catheter 50. It should be understood that various additional interfaces can be incorporated in the guiding catheter.

The inner catheter 50 is comprised of an elongated central shaft 53, an electrode assembly 54 attached to the distal end of the central shaft, and a second handle 56 attached to the proximal end of the central shaft 53. The inner catheter is removably disposed within the guiding catheter, allowing the inner catheter to be removed and reinserted into the guiding catheter a number of times during a medical procedure.

The second handle 56 is comprised of a second mechanism 55 for articulating the distal end of the inner catheter 50, an RF interface 58 for connecting the inner catheter 50 to an RF generator, and a second fluid inter face 57. The second fluid interface is connected to a separate lumen within the inner catheter that extends to the distal end of the inner catheter, providing a conduit for fluids from the second fluid interface to the electrode assembly 54. It should also be understood that various additional interfaces can be incorporated in the inner catheter design.

Figure 2:
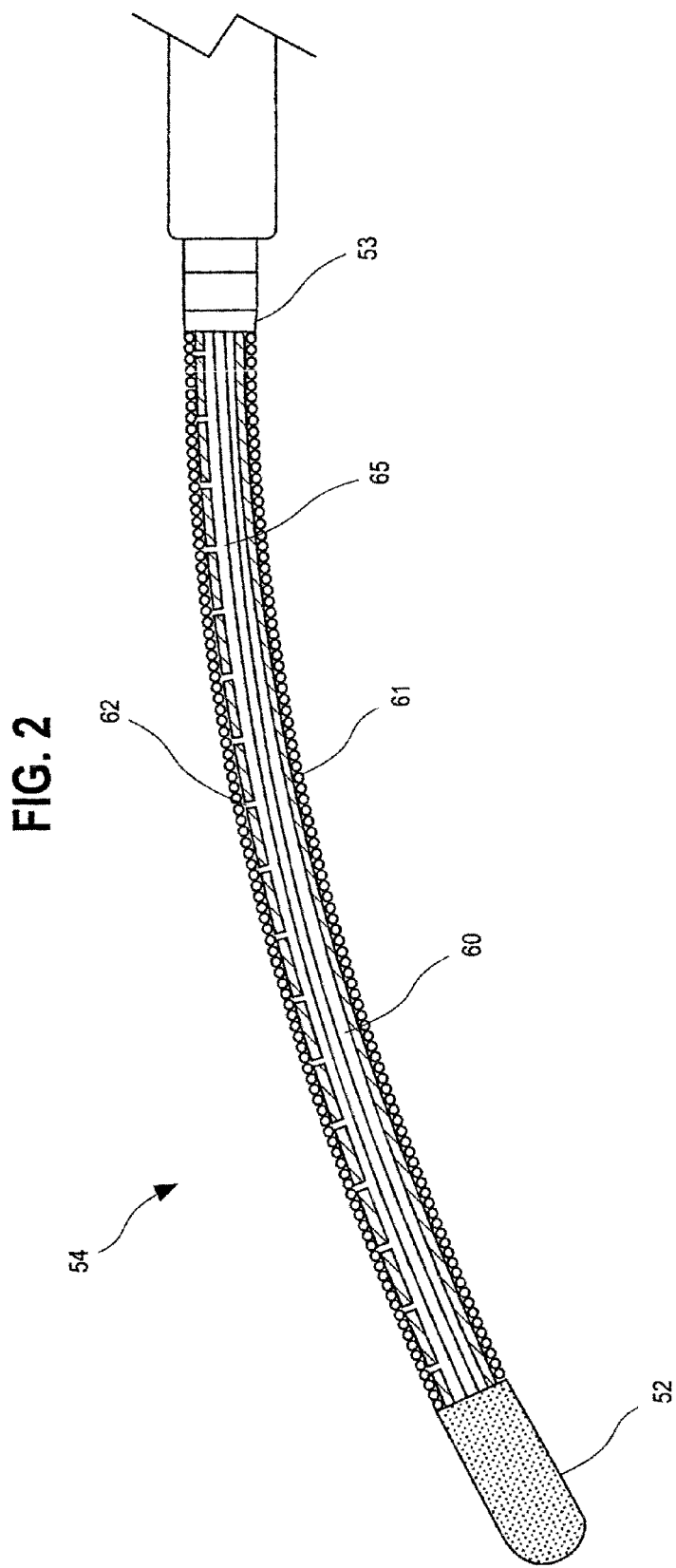
FIG. 2 is a side section view of the distal portion of the ablation catheter shown in FIG. 1 providing an enlarged view of the electrode assembly.

Referring to FIG. 2, the electrode assembly 54 is comprised of a flexible plastic catheter tube 60 having an outer surface, a porous tip electrode 52 attached on the outer surface at the distal end of the catheter tube 60, and at least one linear electrode 61 carried on the outer surface of the catheter tube 60.

The catheter tube 60 is used to provide axial and radial stability to the electrode assembly and to provide a conduit for the flow of fluid to cool the linear electrode 61 and tip electrode 52. The catheter tube 60 is preferably a thin walled, non conductive, single lumen tube constructed of a flexible polymer plastic. Fluid received from the second fluid interface flows through the inner catheter 50 to the catheter tube 60. There the fluid is distributed to the linear electrode 61 and the tip electrode 52 through a plurality of apertures 62 extending from the inner surface of the catheter tube 60 to the outer surface of the catheter tube 60. The apertures 62 are spaced to allow for uniform flow of fluid to all parts of the linear electrode 61 and the porous tip electrode 52. During a RFA procedure, "hot spots" may develop on sections of an electrode if there is not enough fluid flow reaching the area. Since fluid is being uniformly delivered to all sections of the linear electrode 61 and tip electrode 52 through the catheter tube 60, the chances for a "hot spot" to develop is minimized or eliminated.

Figure 5:
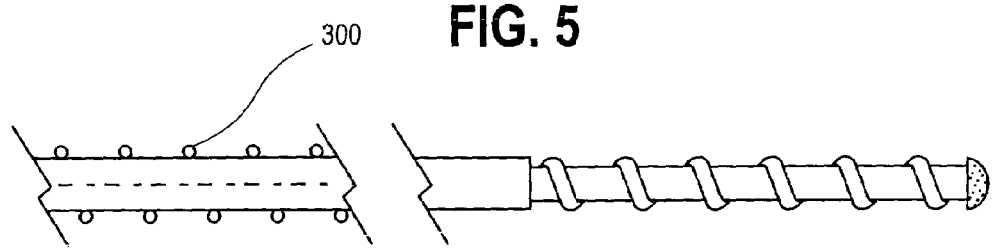
FIG. 5 is a side section view of a linear electrode assembly utilizing coils made of hypodermic tubing.
Figure 6:
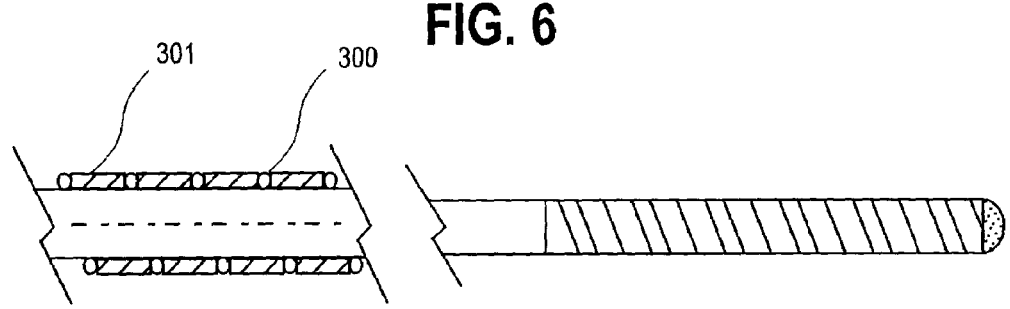
FIG. 6 is a side section view of a linear electrode assembly utilizing coils made of a combination of hypodermic tubing and solid wire.

The linear electrode 61 is utilized in order to make linear lesions in the heart tissue. The linear electrode can be attached either to the elongated central shaft 53 or the catheter tube 60. Conductive wire connects the linear electrode to the RF interface 58. The linear electrode 61 is comprised of a tubular array of conductive metal strands carried on the outer surface of the catheter tube 60, the conductive strands extending along the catheter tube 60 in a plurality of directions relative to the longitudinal axis of the catheter tube 60. The conductive strands are preferably made from rounded or flat solid wire 311, or hypodermic tubing 300, or a combination of both as shown in FIGS. 5 and 6. Hypodermic tubing has the advantage of enabling the linear electrode 61 to be cooled by circulating fluid within the hypodermic tubing as well as from fluid flow from the apertures 62 in the catheter tube 60.

Referring to FIG. 3, in one embodiment, the tubular array of metal strands is a wound helical coil 200. The spacing between loops in the coil is varied in order to achieve different physiological effects. The loops can be wound tightly with each loop in the coil in contact with its neighboring loops as in FIG. 3 or the loops can be wound loosely as in FIG. 5. A tight spacing of the loops in the coil will enable the linear electrode 61 to deliver a higher energy density, but may increase the stiffness of the linear electrode and may increase parasitic power loss. Greater spacing between the loops in the coil will provide more flexibility and less power loss. Referring to FIG. 4 in an alternate embodiment, the tubular array of metal strands is arranged in a braided construction 201.

Figure 7:
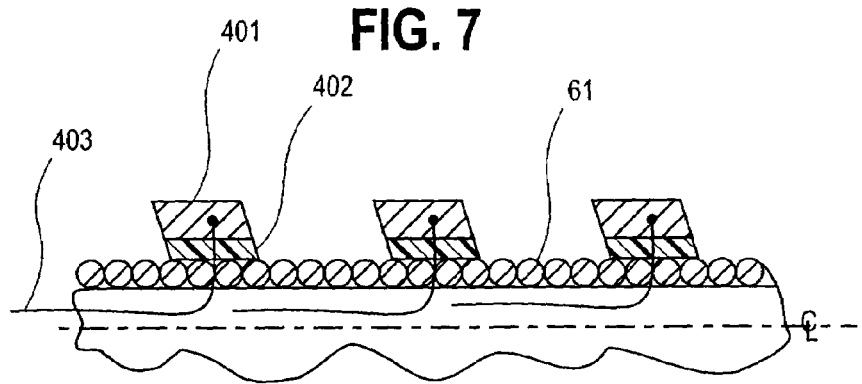
FIG. 7 is a side section view of a linear electrode assembly with added monitoring capabilities.
Figure 8:
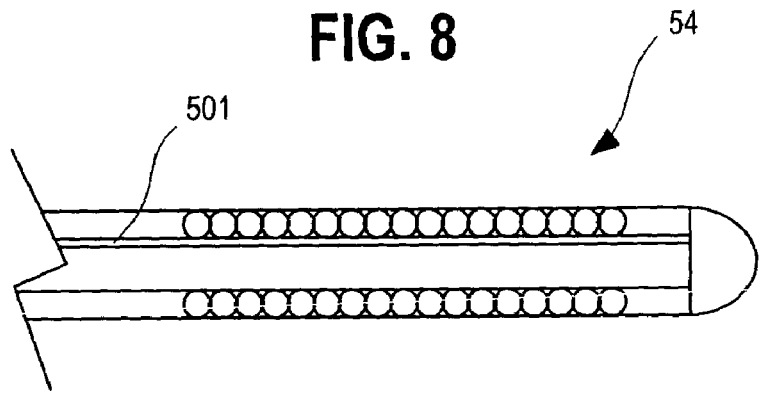
FIG. 8 is side section view of a linear electrode assembly having an articulating means.

Referring to FIG. 7, in order to add more precise electrocardiac mapping capability, additional monitoring electrodes 401 can be placed onto the linear electrode 61. The monitoring electrodes would preferably rest on an insulating sleeve 402 electrically isolated from the linear electrode. The monitoring electrodes are preferably cylindrical metallic bands 401. The metallic bands 401 are coupled to physiological monitoring equipment through a wire 403 extending from the metallic band and through the inner catheter.

Referring to FIG. 2, the porous tip electrode 52 is located at the distal end of the electrode assembly 54. The porous tip electrode 52 provides the inner catheter 50 a means for creating lesions concentrated at particular points in the heart, otherwise called focal lesions. RF energy is supplied to the porous tip electrode through a conductor wire 65 which extends from the tip electrode 52 to the RF interface 58 in the second handle 56.

Referring to FIGS. 1, 2, 8, and 9, articulation of the electrode assembly is utilized in order to better align the linear electrode 61 to the generally arcuate shape of the inner chambers of the heart. One means for articulating the electrode assembly is by extending a pull wire 501 from the second mechanism for articulating 55 through the inner catheter 50 and attaching it to the distal tip of the catheter tube 60. Creating a pulling motion on the pull wire 501 by means of the second mechanism for articulating 55 will cause the distal end of the catheter tube 60 to deflect towards the direction of the pulling motion. A stiffener can be used in this configuration in order to return the electrode assembly 54 back to its original position.

Figure 9:
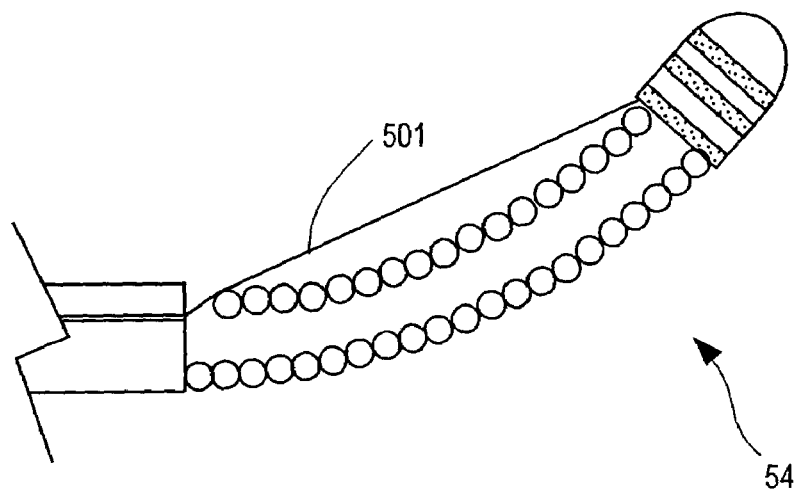
FIG. 9 is a side section view of a linear electrode assembly having an exterior articulating means.

Referring to FIG. 9, an alternate means for articulating the electrode assembly is achieved by running the pull wire 501 from the second mechanism for articulating 55 through the inner catheter 50, then having the wire run externally along the linear electrode, and then finally attaching the pull wire 501 to the distal tip of the electrode assembly 54.

Figure 10:
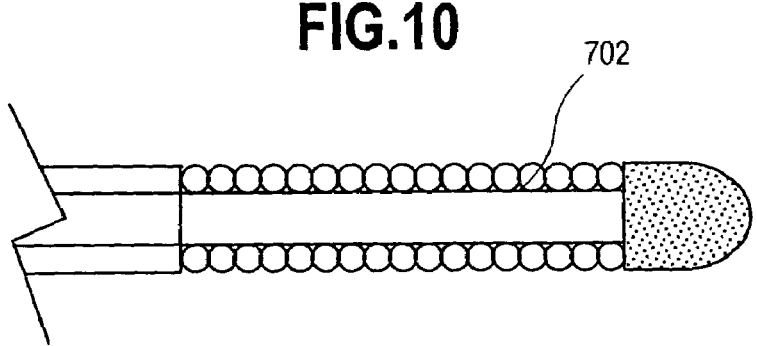
FIG. 10 is side section view of a linear electrode assembly having a thermally activated alternative articulating means.

Referring to FIG. 10, a second alternate means for articulating the electrode assembly is achieved through the use of a memory shaped tube 702 which is thermally activated to conform to a predetermined shape. Nitinol™ tubing or other materials having thermally activated shape memory characteristics can be used for the catheter tube 60. The catheter tube would remain relatively erectile during the positioning of the electrode assembly 54, but once the RF energy is applied, the thermal energy would cause the Nitinol™ tubing to deflect into an arcuate shape. This means for articulation has the advantage of not requiring the use of pull wires 501 or mechanisms for articulating.

It can be seen that the ablation catheter which has been provided above allows for greater choice in the type of lesions which can be made, also allows for greater maneuverability, more precise placement, and better cooling of the electrodes. Although illustrative embodiments of the invention have been shown and described, it is not intended that the novel device be limited thereby. It is to be understood that this novel invention may be susceptible to modifications and variations that are within the scope and fair meaning of the accompanying claims and drawings.

What is claimed:

1. An ablation catheter which comprises:
a guiding catheter; and
an inner catheter disposed within said guiding catheter, said inner catheter comprising an elongated central shaft having a distal end, and an electrode assembly attached to the distal end of said elongated central shaft and having a distal tip, said electrode assembly comprising a catheter tube having a plurality of apertures therethrough, a linear ablation electrode, said linear ablation electrode being continuous and axially elongated relative to its width, a porous tip ablation electrode at said distal tip, and a device for articulating said electrode assembly.

2. The catheter of claim 1 wherein said linear electrode is made from a combination of hypodermic tubing and solid wire.

3. The catheter of claim 1 further comprising monitoring electrodes nonconductively mounted on said linear electrode.

4. The catheter of claim 1 wherein the articulating device comprises at least one pull wire attached to a distal end of said electrode assembly.

5. The catheter of claim 1 wherein said catheter tube is made from shape memory tubing, thereby allowing said catheter tube to bend to a predetermined shape upon the application of radio frequency energy.

6. The catheter of claim 1, positioned within a lumen of an outer guiding catheter, said guiding catheter having a guiding catheter articulating mechanism.

7. The catheter of claim 1 in which said linear electrode comprises a tubular array of conductive metal strands car ried by said inner catheter, said inner catheter defining a plurality of apertures to permit the flow of cooling fluid from a lumen of the inner catheter and through said apertures, to flow among said conductive metal strands.

8. The catheter of claim 1 in which said inner catheter has a first steering mechanism and said guiding catheter has a second steering mechanism.

9. The catheter of claim 8 in which said linear electrode comprises a tubular array of connected metal strands carried by said inner catheter, said inner catheter defining a plurality of apertures to permit the flow of cooling fluid from a lumen of the inner catheter and through said apertures, to flow among said conductive metal strands.

10. The catheter of claim 2 in which said linear electrode comprises a tubular array of conductive metal strands carried by said inner catheter, said inner catheter defining a plurality of apertures to permit the flow of cooling fluid from a lumen of the inner catheter and through said apertures, to flow among said conductive metal strands.

* * * * *